(12) United States Patent
Han et al.

(10) Patent No.: US 9,227,941 B2
(45) Date of Patent: Jan. 5, 2016

(54) CARBON NANOMATERIAL HAVING HIGHER ORDER STRUCTURE BY MEANS OF MULTIPLE HYDROGEN BONDS AND METHOD FOR PREPARING SAME

(75) Inventors: Joong-tark Han, Changwon-si (KR); Geon-woong Lee, Changwon-si (KR); Seung-yol Jeong, Changwon-si (KR); Hee-jin Jeong, Changwon-si (KR); Bo hwa Jeong, Changwon-si (KR)

(73) Assignee: Korea Eletrotechnology Research Institute, Changwon-si, Gyeongsangnam-do (KR)

( * ) Notice: Subject to any disclaimer, the term of this patent is extended or adjusted under 35 U.S.C. 154(b) by 0 days.

(21) Appl. No.: 14/415,879

(22) PCT Filed: May 9, 2012

(86) PCT No.: PCT/KR2012/003622
§ 371 (c)(1),
(2), (4) Date: Jan. 20, 2015

(87) PCT Pub. No.: WO2013/154224
PCT Pub. Date: Oct. 17, 2013

(65) Prior Publication Data
US 2015/0218108 A1    Aug. 6, 2015

(30) Foreign Application Priority Data
Apr. 10, 2012    (KR) .................... 10-2012-0037478

(51) Int. Cl.
| | |
|---|---|
| *C07D 239/22* | (2006.01) |
| *C01B 31/02* | (2006.01) |
| *C09D 5/24* | (2006.01) |
| *H01B 1/12* | (2006.01) |
| *B82Y 40/00* | (2011.01) |
| *B82Y 30/00* | (2011.01) |

(52) U.S. Cl.
CPC .......... *C07D 239/22* (2013.01); *C01B 31/0273* (2013.01); *C09D 5/24* (2013.01); *H01B 1/12* (2013.01); *B82Y 30/00* (2013.01); *B82Y 40/00* (2013.01)

(58) Field of Classification Search
CPC .................................................. C07D 239/22
USPC ....................................................... 544/319
See application file for complete search history.

(56) References Cited

U.S. PATENT DOCUMENTS

| | | |
|---|---|---|
| 2007/0298669 A1 | 12/2007 | Barrera et al. |
| 2008/0093224 A1 | 4/2008 | Tour et al. |
| 2010/0247381 A1 | 9/2010 | Yodh et al. |

FOREIGN PATENT DOCUMENTS

| | | |
|---|---|---|
| KR | 10-0685796 B1 | 2/2007 |
| KR | 10-2010-0025178 A | 3/2010 |

OTHER PUBLICATIONS

WIPO, International Search Report (PCT/KR2012/003622), Mar. 21, 2013.
Akshay Kokil et al., Introduction of Multiple Hydrogen Bonding for Enhanced Mechanical Performance of Polymer-Carbon Nanotube Composites, Jounal of Macromolecular Science, Part A: Pure and Applied Chemistry, Nov. 1, 2011.

*Primary Examiner* — Taofiq A Solola
(74) *Attorney, Agent, or Firm* — Park & Associates IP Law, P.C.

(57) ABSTRACT

The present invention relates to a carbon nanomaterial having a higher order structure by means of multiple hydrogen bonds and to a method for preparing same. One of the key technical features of the present invention is a carbon nanomaterial having a higher order structure, in which a functional group capable of multiple hydrogen bonds reacts with a conductive carbon nanomaterial, into which said functional group is introduced by a surface modification to be functionalized, thus enabling multiple hydrogen bonds between carbon nanomaterials. In addition, another of the key technical features of the present invention is a method for preparing a carbon nanomaterial having a higher order structure by means of multiple hydrogen bonds, comprising: a first step of modifying the surface of a carbon nanomaterial to introduce a functional group for multiple hydrogen bonds into a conductive carbon nanomaterial; a second step of introducing a functional group capable of multiple hydrogen bonds by the reaction with the carbon nanomaterial functionalized in the first step; and a third step of preparing a paste using the carbon nanomaterial of the second step into which the multiple hydrogen bonds are introduced. As described above, a functional group capable of three or more multiple hydrogen bonds is introduced into a conductive carbon nanomaterial such as a carbon nanotube, graphene, carbon fiber or carbon black, thus inducing the formation of a supramolecular structure between materials and thus enabling the carbon nanomaterial of the present invention to be used for printed electronics. Furthermore, the carbon nanomaterial of the present invention can be utilized as an electrode for an energy storage element such as a secondary battery or a super capacitor when formed into a sheet-type conductive membrane, and can be applied for manufacturing conductive fibers.

9 Claims, 5 Drawing Sheets

(a)

(b)

(c)

CARBON NANOMATERIAL HAVING HIGHER ORDER STRUCTURE BY MEANS OF MULTIPLE HYDROGEN BONDS AND METHOD FOR PREPARING SAME

REFERENCE TO RELATED APPLICATIONS

This application is a U.S. National Phase application of International Application No. PCT/KR2012/003622 filed on May 9, 2012, which designates the United States and claims priority of Korean Patent Application No. 10-2012-0037478 filed on Apr. 10, 2012, the disclosures of each of these applications being incorporated herein by reference in their entireties.

FIELD OF THE INVENTION

The present invention relates to a carbon nanomaterial having a higher order structure through multiple hydrogen bonding and a method of preparing the same. More particularly, the present invention relates to a carbon nanomaterial having a higher order structure through multiple hydrogen bonding, and a method of preparing the same, wherein a conductive carbon nanomaterial, such as carbon nanotubes, graphene, carbon fibers, and carbon black, is introduced with a functional group able to form at least three multiple hydrogen bonds, thereby enabling the formation of a supramolecular carbon nanomaterial.

BACKGROUND OF THE INVENTION

Typically, a conductive carbon nanomaterial, such as carbon nanotubes, graphene, and carbon fibers, is applied to the manufacture of items in a variety of fields, including transparent electrodes, electrode materials for antistatic, electromagnetic shielding and energy storage devices, and conductive fibers. A paste type coating solution or spinning dope is required for a coating process or a fiberizing process.

Essentially useful to prepare a coating solution or a paste is a dispersant, such as a surfactant, a copolymer or an ionic liquid. In the case where a functional group is excessively introduced to the surface of a material, dispersion becomes easy but poor conductivity may result.

Hence, when a conductive carbon nanomaterial is prepared into a conductive paste while maintaining conductivity without the use of a dispersant, the preparation cost may be reduced and the preparation process may be simplified. Also, since the use of a dispersant is obviated, the carbon nanomaterial may be combined with various binders and metals or metal oxides.

However, formation of a carbon nanomaterial having a higher order structure by introducing a functional group able to form at least three multiple hydrogen bonds has not yet been reported.

SUMMARY OF THE INVENTION

Accordingly, the present invention has been made keeping in mind the problems occurring in the related art, and an object of the present invention is to provide a carbon nanomaterial having a higher order structure through multiple hydrogen bonding, and a method of preparing the same, wherein a conductive carbon nanomaterial, such as carbon nanotubes, graphene, carbon fibers, and carbon black, is introduced with a functional group able to form at least three multiple hydrogen bonds, thus enabling the formation of a supramolecular carbon nanomaterial.

In order to accomplish the above object, the present invention provides a carbon nanomaterial having a higher order structure through multiple hydrogen bonding, configured such that a conductive carbon nanomaterial functionalized by surface modification is reacted with a functional group for multiple hydrogen bonding, thus forming a multiple hydrogen-bonded carbon nanomaterial.

In addition, the present invention provides a method of preparing a carbon nanomaterial having a higher order structure through multiple hydrogen bonding, comprising: 1) modifying the surface of a conductive carbon nanomaterial to introduce a functional group for multiple hydrogen bonding, thus obtaining a functionalized carbon nanomaterial; 2) reacting the functionalized carbon nanomaterial with the functional group for multiple hydrogen bonding, thus forming a multiple hydrogen-bonded carbon nanomaterial; and 3) preparing a paste using the multiple hydrogen-bonded carbon nanomaterial.

The carbon nanomaterial preferably includes at least one selected from among carbon nanotubes, carbon fibers, graphene, and carbon black.

The surface modification is preferably performed using at least one process selected from among acid treatment, supercritical water treatment, UV-ozone treatment, and plasma treatment.

The functional group for multiple hydrogen bonding preferably includes at least one selected from among a 2-ureido-4[1H]pyrimidinone derivative, a 2-ureido-4[1H]pyrimidinol derivative, a 2-uriedo-4-pyrimidone derivative, a diacylpyrimidine derivative, a ureidoacylpyrimidine derivative, an acetylaminotriazine derivative, a ureidotriazine derivative, a 2,6-di(acetylamino)-4-pyridyl derivative, a thymine derivative, a 2-aminobenzimidazole derivative, a 2,7-diamino-1,8-naphthyridine derivative, a di(hexanoylamino)pyrimidine derivative, and a 2-butylureido-4-acetylaminopyridine derivative.

The carbon nanomaterial is preferably provided in the form of a paste.

Therefore, as a conductive carbon nanomaterial, such as carbon nanotubes, graphene, carbon fibers, and carbon black, is introduced with a functional group able to form at least three multiple hydrogen bonds, the formation of a supramolecular carbon nanomaterial may be induced. Hence, such a carbon nanomaterial may be used for printed electronic electrodes and electromagnetic shielding materials. It can also be utilized in electrodes for energy production and storage devices, such as solar cells, secondary batteries, fuel cells, and supercapacitors. Furthermore, the carbon nanomaterial is effective in manufacturing conductive fibers.

According to the present invention, a conductive carbon nanomaterial, such as carbon nanotubes, graphene, carbon fibers, and carbon black, is introduced with a functional group able to form at least three multiple hydrogen bonds, thereby enabling the formation of a supramolecular carbon nanomaterial. Therefore, such a carbon nanomaterial can be used for printed electronic electrodes and electromagnetic shielding materials. It can also be utilized in electrodes for energy production and storage devices, such as solar cells, secondary batteries, fuel cells, and supercapacitors. Furthermore, the carbon nanomaterial can be effectively applied to manufacturing conductive fibers.

DETAILED DESCRIPTION OF THE INVENTION

Hereinafter, a detailed description will be given of preferred embodiments of the present invention, with reference to the appended drawings.

Figure 1:
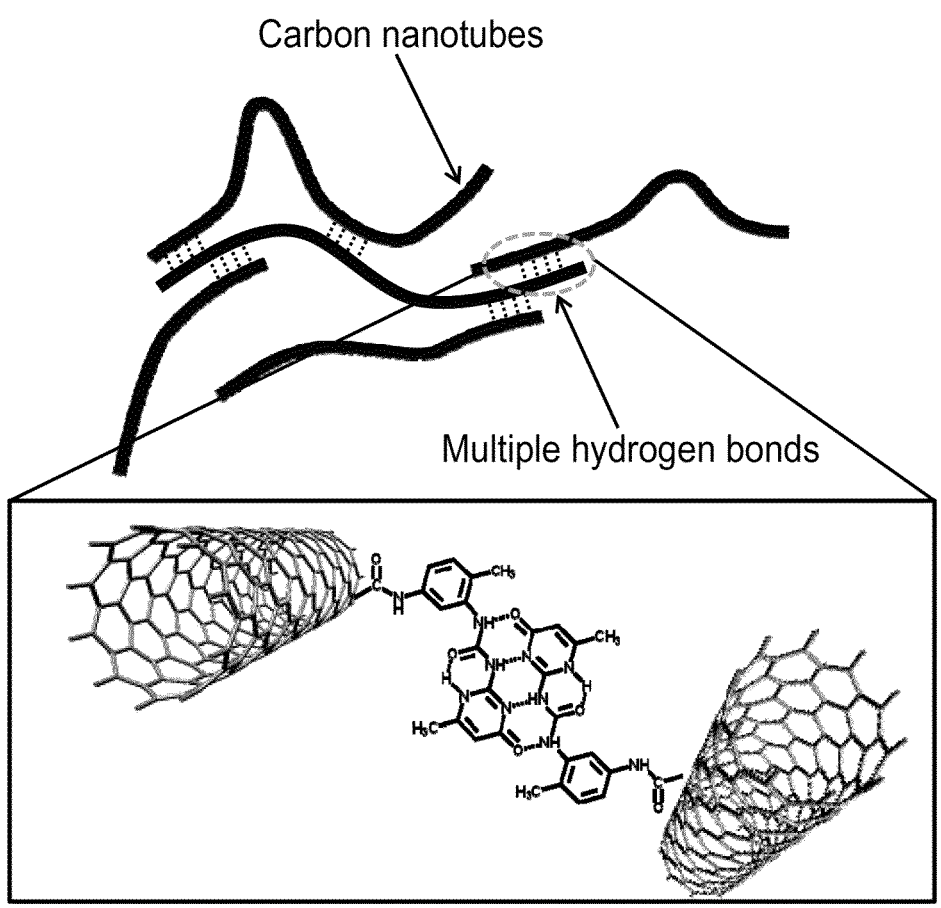
FIG. 1 schematically illustrates multiple hydrogen bonds introduced to a carbon nanomaterial according to an embodiment of the present invention.
Figure 2:
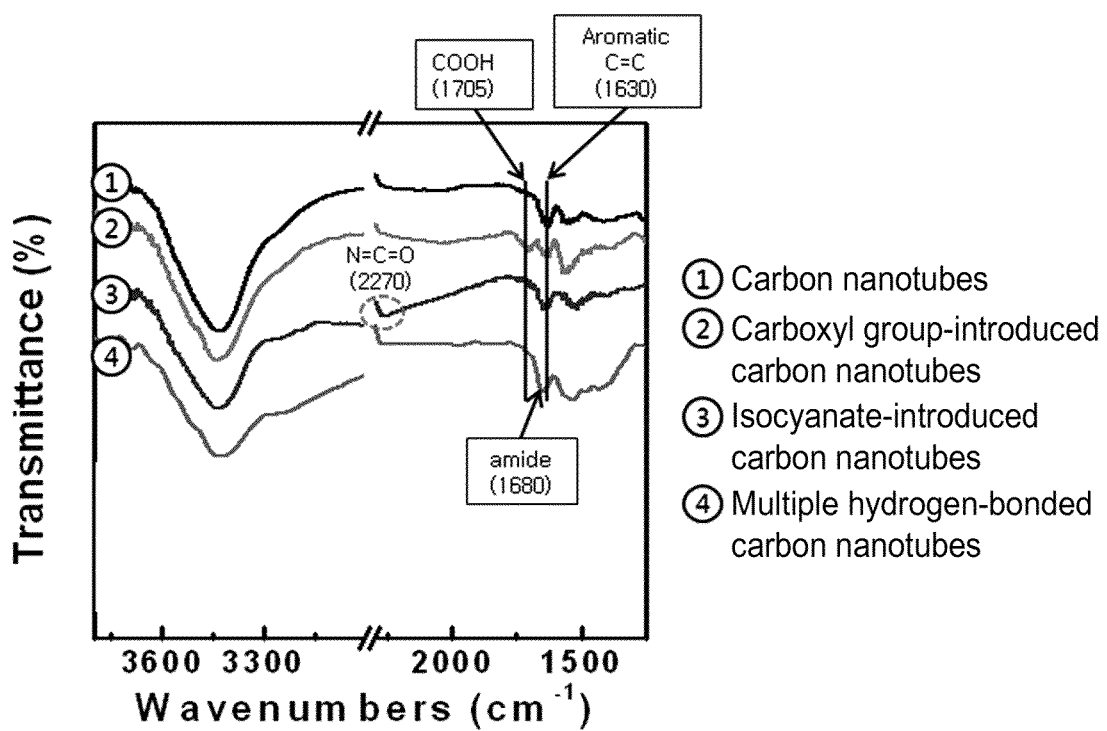
FIG. 2 illustrates infrared spectroscopy spectrum per functionalization step according to an embodiment of the present invention.
Figure 3:
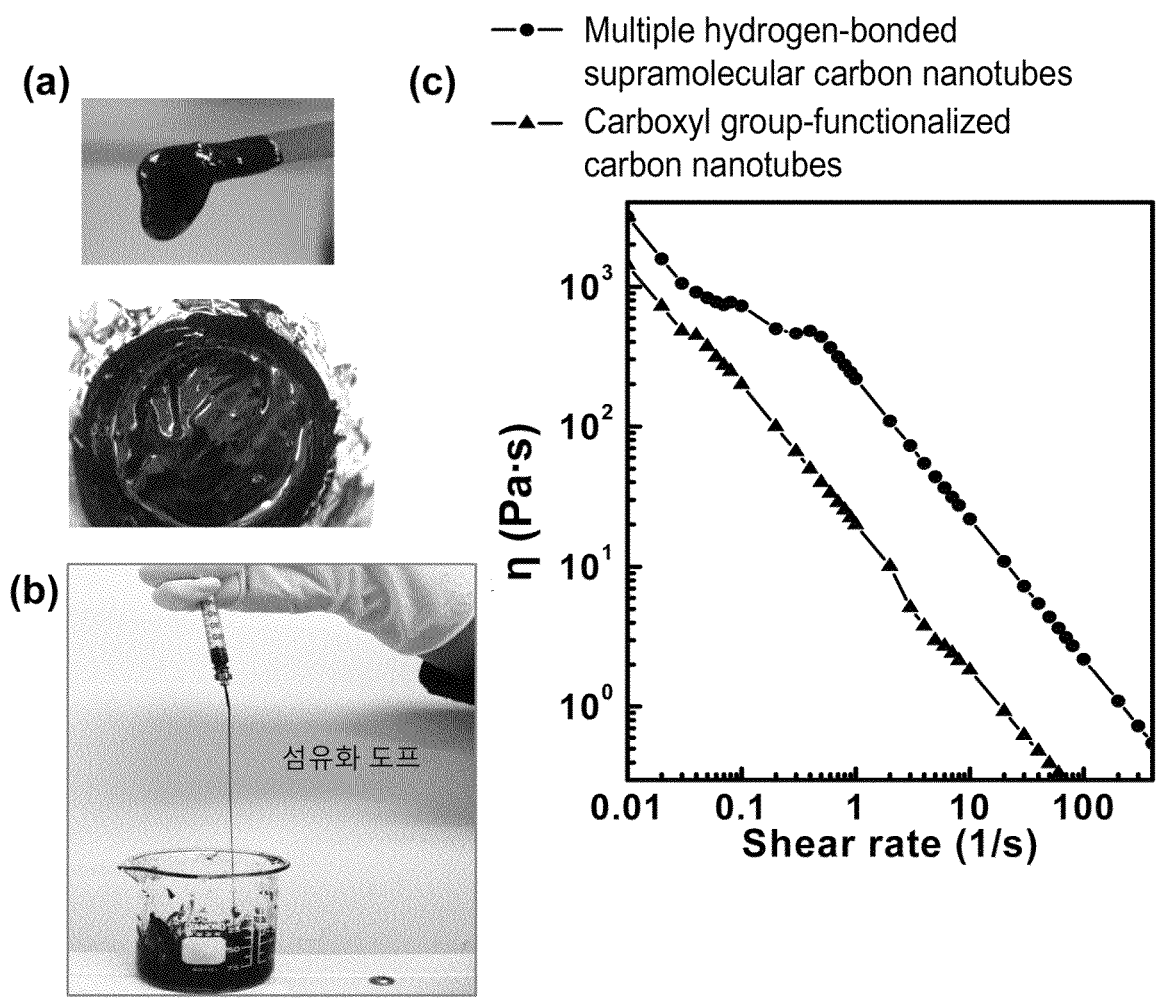
FIG. 3(a) illustrates a paste formed according to the present invention.
FIG. 3(b) illustrates a spinnable dope.
FIG. 3(c) illustrates the measurement results of viscosity of the paste.
Figure 4:
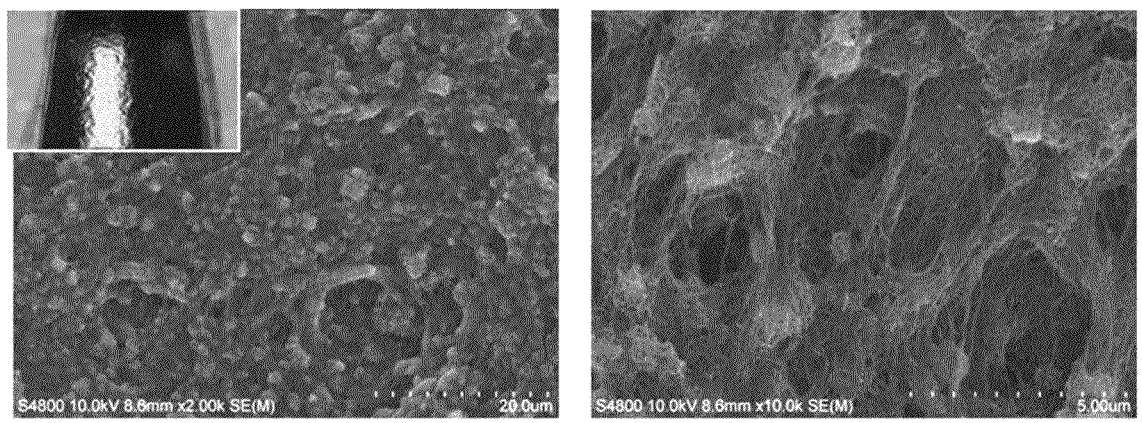
FIG. 4 illustrates surface morphology of a coating film formed using multiple hydrogen-bonded carbon nanotubes according to an embodiment of the present invention.
Figure 5:
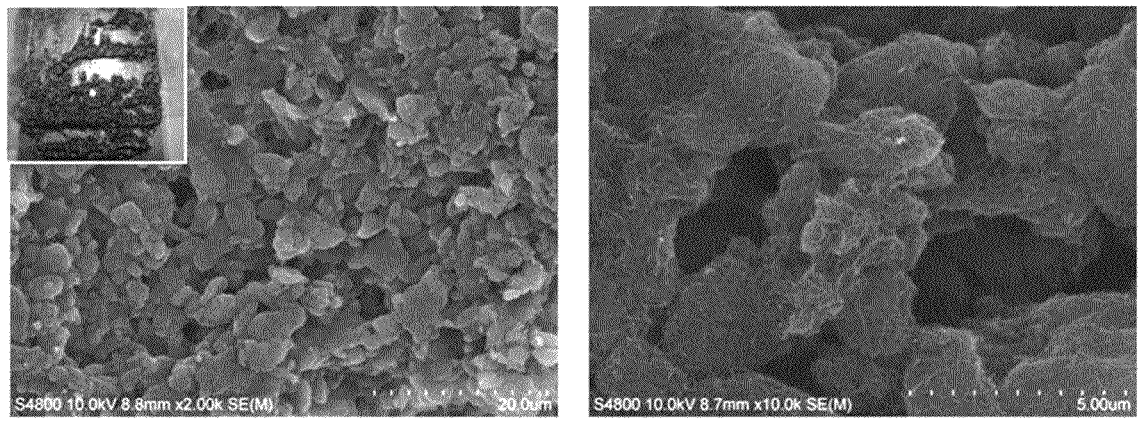
FIG. 5 illustrates surface morphology of a coating film formed using carbon nanotubes functionalized with only a carboxyl group according to a comparative embodiment.

FIG. 1 schematically illustrates multiple hydrogen bonds introduced to a carbon nanomaterial according to an embodiment of the present invention; FIG. 2 illustrates infrared spectroscopy spectrum per functionalization step according to an embodiment of the present invention; FIG. 3(a) illustrates a paste formed according to the present invention, FIG. 3(b) illustrates a spinnable dope, and FIG. 3(c) illustrates the measurement results of viscosity of the paste; FIG. 4 illustrates surface morphology of a coating film formed using multiple hydrogen-bonded carbon nanotubes according to an embodiment of the present invention; FIG. 5 illustrates surface morphology of a coating film formed using carbon nanotubes functionalized with only a carboxyl group according to a comparative embodiment; and FIG. 6(a) illustrates a flexible carbon nanotube sheet manufactured using multiple hydrogen-bonded carbon nanotubes according to an embodiment of the present invention, FIG. 6(b) illustrates a conductive pattern formed on a polymer substrate, and FIG. 6(c) illustrates conductive fibers.

As illustrated in the drawings, a method of manufacturing a carbon nanomaterial having a higher order structure through multiple hydrogen bonding according to the present invention includes: 1) modifying the surface of a conductive carbon nanomaterial to introduce a functional group for multiple hydrogen bonding, thus forming a functionalized carbon nanomaterial; 2) reacting the functionalized carbon nanomaterial with the functional group for multiple hydrogen bonding, thus obtaining a multiple hydrogen-bonded carbon nanomaterial; and 3) preparing a paste using the multiple hydrogen-bonded carbon nanomaterial. This method is specified below.

The multiple hydrogen bonding includes a hydrogen bond donor (D), a hydrogen bond acceptor (A), and an ionic hydrogen bond donor (D+). For triple hydrogen bonding, D, D+ and A are arrayed into ADA-DAD, ADD-DAA, AAA-DDD, and cationic AAA-DDD+ pairs. For quadruple hydrogen bonding, at least one array of ADAD-DADA, AADD-DDAA, ADDA-DAAD, AAAD-DDDA, ADAA-DADD, AAAA-DDDD, and cationic AAAA-DDD+ pairs is preferably introduced.

The functional group that allows the above hydrogen bonding may include at least one selected from among 2-ureido-4[1H]pyrimidinone derivative, a 2-ureido-4[1H]pyrimidinol derivative, a 2-uriedo-4-pyrimidone derivative, a diacylpyrimidine derivative, a ureidoacylpyrimidine derivative, an acetylaminotriazine derivative, a ureidotriazine derivative, a 2,6-di(acetylamino)-4-pyridyl derivative, a thymine derivative, a 2-aminobenzimidazole derivative, a 2,7-diamino-1,8-naphthyridine derivative, a di(hexanoylamino)pyrimidine derivative, and a 2-butylureido-4-acetylaminopyridine derivative.

1st Embodiment

A first embodiment of the present invention addresses a method of introducing carbon nanotubes with a functional group for quadruple hydrogen bonding.

The structure of a functional group for quadruple hydrogen bonding is schematically illustrated in FIG. 1.

Specifically, 10 g of multi-walled carbon nanotubes is mixed with 200 mL of a mixed solution of sulfuric acid and nitric acid (7:3 volume ratio), heated to 80° C., stirred for 24 hr, and then cooled to room temperature.

Subsequently, the resulting mixture is diluted with 800 mL of distilled water. The diluted solution is filtered at least four times using filter paper to remove the acid solution from the carbon nanotubes, and then dried, thus obtaining multi-walled carbon nanotubes having a carboxyl group (—COOH) introduced thereto.

The carbon nanotubes having a carboxyl group (—COOH) introduced thereto are dispersed at 100 mg/L in a dimethylformamide solvent, and then reacted in a manner that is mixed with toluene diisocyanate and stirred at 100° C. for 12 hr, thereby introducing an isocyanate group.

Subsequently, the carbon nanotubes having an isocyanate group introduced thereto are mixed with amino-4-hydroxy-6-methyl-pyrimidine, and stirred at 100° C. for 20 hr, thereby introducing quadruple hydrogen bonding 2-ureido-4[1H]pyrimidinone units.

FIG. 2 illustrates infrared spectroscopy spectrum per functionalization step. As illustrated in FIG. 2, the spectrum of the multiple hydrogen-bonded carbon nanotubes is broad compared to the other spectra, which means that many hydrogen bonds are present in the carbon nanotubes.

The multiple hydrogen-bonded supramolecular carbon nanotubes thus prepared are formed into a paste by simple stirring in the presence of a dimethylformamide solvent, without the use of other additives. As illustrated in FIG. 3, a carbon nanotube paste having a solid content of 0.5 wt % or more may be easily prepared by simple stirring. Based on the measurement results of viscosity of the paste, as indirectly evaluated in FIG. 3(c), the viscosity is increased in a small shear stress range, and thereby the carbon nanotubes are interconnected through multiple hydrogen bonding, resulting in a supramolecular structure.

In order to compare the surface morphology of the supramolecular carbon nanotubes as the carbon nanomaterial having a higher order structure through multiple hydrogen bonding according to the present invention, a comparative carbon nanotube paste functionalized with only a carboxyl group is prepared, which will be described below.

Comparative Embodiment

Comparative multi-walled carbon nanotubes having a carboxyl group merely acid-treated with a sulfuric acid/nitric acid mixed solution as in the first embodiment are prepared to form a paste. The comparative multi-walled carbon nanotubes cannot be prepared into a paste, unlike the multiple hydrogen-bonded supramolecular carbon nanotubes.

FIG. 4 illustrates surface morphology of a coating film formed using the multiple hydrogen-bonded carbon nanotubes according to the first embodiment of the present invention, and FIG. 5 illustrates surface morphology of a coating film formed using the carbon nanotubes functionalized with only a carboxyl group according to the comparative embodiment. As illustrated in FIG. 5, since the carbon nanotubes functionalized with a carboxyl group are not prepared into a paste, they are forcibly applied, and thus the carbon nanotubes are poorly dispersed and are thus present in the form of a tangled clump. On the other hand, as illustrated in FIG. 4, the multiple hydrogen-bonded supramolecular carbon nanotubes are configured such that the carbon nanotubes are interconnected through multiple hydrogen bonding, thus forming a rigid film.

Figure 6:
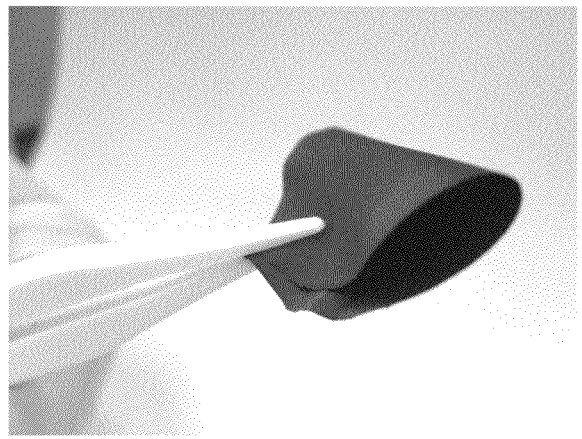
FIG. 6(a) illustrates a flexible carbon nanotube sheet manufactured using multiple hydrogen-bonded carbon nanotubes according to an embodiment of the present invention.
FIG. 6(b) illustrates a conductive pattern formed on a polymer substrate.
FIG. 6(c) illustrates conductive fibers.
Figure 6:
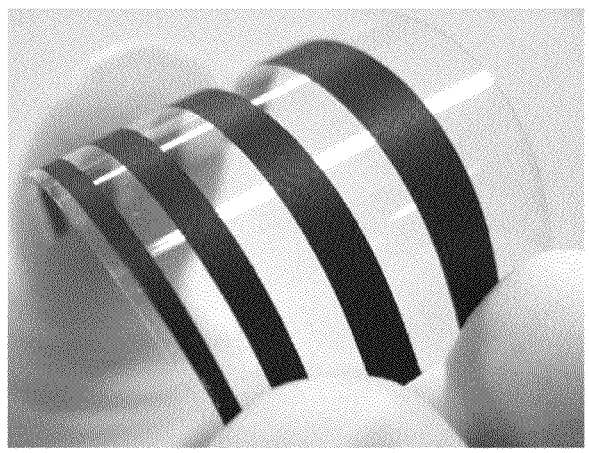
Figure 6:
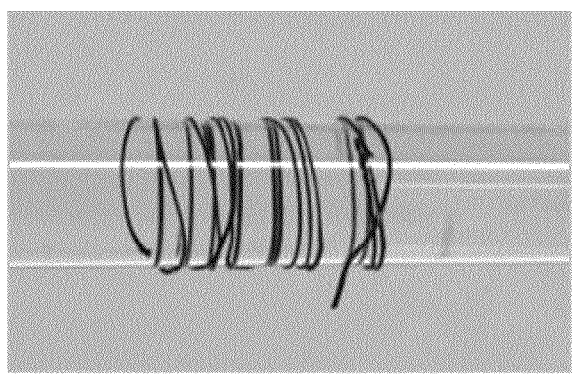

FIG. 6 illustrates a carbon nanotube sheet formed using the supramolecular carbon nanotubes according to the present invention. Also, a conductive pattern may be formed on a polymer substrate, and it is possible to perform spinning into fibers using a paste type spinning dope having a supramolecular structure.

2nd Embodiment

A second embodiment of the present invention addresses a method of introducing graphene with a functional group for quadruple hydrogen bonding.

Specifically, carboxyl group-introduced graphene (graphene oxide) is prepared in such a manner that pure graphite is treated with sulfuric acid and $KMnO_4$ for three days and purified with hydrogen peroxide and hydrochloric acid, giving graphite oxide that is then exfoliated using a sonicator.

The graphene oxide thus prepared is dispersed at a concentration of 500 mg/L in dimethylformamide and then reacted with isocyanate and amino-4-hydroxy-6-methyl pyrimidine as in the first embodiment, thereby introducing a functional group for quadruple hydrogen bonding.

The graphene thus prepared is simply stirred, thus preparing a paste having a solid content of 10%, which is then added with hydrazine ($N_2H_4$), stirred at 100° C. for 12 hr, and reduced.

When the reduced graphene paste is applied on a plastic substrate, a high conductivity of 5000 S/m or more may result.

The present invention pertains to a carbon nanomaterial having a higher order structure through multiple hydrogen bonding, and a method of preparing the same. More particularly, the present invention relates to a carbon nanomaterial having a higher order structure through multiple hydrogen bonding, and a method of preparing the same, wherein a conductive carbon nanomaterial, such as carbon nanotubes, graphene, carbon fibers, and carbon black, is introduced with a functional group able to form at least three multiple hydrogen bonds, thereby enabling the formation of a supramolecular carbon nanomaterial.

What is claimed is:

1. A supramolecular carbon nanomaterial, comprising functionalized conductive carbon nanomaterials interconnected through at least one of a triple array and a quadruple array of hydrogen bonds, wherein the functionalized conductive carbon nanomaterials are introduced with a functional group selected from the group consisting of 2-ureido-4[1H] pyrimidinone, 2-ureido-4[1H]pyrimidinol, 2-uriedo-4-pyrimidone, diacylpyrimidine, ureidoacylpyrimidine, acetylaminotriazine, ureidotriazine, 2,6-di(acetylamino)-4-pyridyl, thymine, 2-aminobenzimidazole, 2,7-diamino-1,8-naphthyridine, di(hexanoylamino)pyrimidine, and 2-butylureido-4-acetylaminopyridine for multiple hydrogen bonding.

2. The supramolecular carbon nanomaterial of claim 1, wherein the functionalized carbon nanomaterial is one of carbon nanotubes, carbon fibers, graphene, and carbon black.

3. The supramolecular carbon nanomaterial of claim 1, wherein the supramolecular carbon nanomaterial is provided in a paste form.

4. A method of preparing a supramolecular carbon nanomaterial, comprising:
preparing a conductive carbon nanomaterial introduced with a carboxyl group (—COOH);
reacting the conductive carbon nanomaterial having the carboxyl group with toluene diisocyanate in a dimethylformamide solvent, thereby introducing an isocyanate group to the conductive carbon nanomaterial; and
introducing a functional group for multiple hydrogen bonding to the conductive carbon nanomaterial introduced with the isocyanate group, wherein the functional group for multiple hydrogen bonding is selected from the group consisting of 2-ureido-4[1H]pyrimidinone, 2-ureido-4[1H]pyrimidinol, 2-uriedo-4-pyrimidone, diacylpyrimidine, ureidoacylpyrimidine, acetylaminotriazine, ureidotriazine, 2,6-di(acetylamino)-4-pyridyl, thymine, 2-aminobenzimidazole, 2,7-diamino-1,8-naphthyridine, di(hexanoylamino)pyrimidine and 2-butylureido-4-acetylaminopyridine.

5. The method of claim 4, wherein the conductive carbon nanomaterial is one of carbon nanotubes, carbon fibers, graphene and carbon black.

6. The method of claim 4, wherein said conductive carbon nanomaterial is carbon nanotubes, and wherein the step for introducing a functional group for multiple hydrogen bonding to the conductive carbon nanomaterial is carried out by reacting the conductive carbon nanomaterial having the isocyanate group introduced thereto with amino-4-hydroxy-6-methyl-pyrimidine, thereby obtaining carbon nanotubes introduced with quadruple hydrogen bonding 2-ureido-4[1H] pyrimidinone units.

7. The method of claim 6, further comprising:
stirring the carbon nanotubes introduced with quadruple hydrogen bonding 2-ureido-4[1H]pyrimidinone in the dimethylformamide solvent without adding any additional additives therein to obtain a carbon nanotube paste having a solid content of at least 0.5 wt %.

8. The method of claim 4, wherein said conductive carbon nanomaterial is graphene oxide, and wherein the step for introducing a functional group for multiple hydrogen bonding to the conductive carbon nanomaterial is carried out by reacting the conductive carbon nanomaterial having the isocyanate group introduced thereto with amino-4-hydroxy-6-methyl-pyrimidine, thereby obtaining graphene oxide introduced with quadruple hydrogen bonding 2-ureido-4[1H] pyrimidinone units.

9. The method of claim 8, further comprising:
stirring the graphene oxide introduced with quadruple hydrogen bonding 2-ureido-4[1H]pyrimidinone in the dimethylformamide solvent without adding any additional additives therein to obtain a graphene oxide paste having a solid content of at least 10 wt %;
adding hydrazine ($N_2H_4$);
stirring at 100° C. for 12 hr; and
reducing the graphene to obtain a reduced graphene paste.

* * * * *